US 8,879,069 B2

(12) United States Patent
Okamura et al.

(10) Patent No.: US 8,879,069 B2
(45) Date of Patent: Nov. 4, 2014

(54) OPTICAL IMAGE MEASUREMENT DEVICE

(75) Inventors: Kazuyuki Okamura, Tokyo (JP);
Yasuhisa Ishikura, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 292 days.

(21) Appl. No.: 13/257,525

(22) PCT Filed: Mar. 30, 2010

(86) PCT No.: PCT/JP2010/002301
§ 371 (c)(1),
(2), (4) Date: Sep. 19, 2011

(87) PCT Pub. No.: WO2010/113476
PCT Pub. Date: Oct. 7, 2010

(65) Prior Publication Data
US 2012/0013915 A1     Jan. 19, 2012

(30) Foreign Application Priority Data

Apr. 3, 2009   (JP) .................................. 2009-090915

(51) Int. Cl.
*G01B 9/02*     (2006.01)
*A61B 3/10*     (2006.01)
(52) U.S. Cl.
CPC ..................................... *A61B 3/102* (2013.01)
USPC ......................................................... 356/479
(58) Field of Classification Search
CPC ............................... A61B 3/102; A61B 5/066
USPC .................................................. 356/479, 497
See application file for complete search history.

(56) References Cited

U.S. PATENT DOCUMENTS

| 6,377,349 B1 | 4/2002 | Fercher |
| 6,608,717 B1* | 8/2003 | Medford et al. ............... 359/368 |
| 7,433,046 B2* | 10/2008 | Everett et al. .................. 356/479 |
| 7,480,059 B2* | 1/2009 | Zhou et al. ..................... 356/498 |
| 7,859,680 B2* | 12/2010 | Abe et al. ........................ 356/479 |
| 2008/0239240 A1 | 10/2008 | Tsukada et al. |
| 2009/0027685 A1 | 1/2009 | Abe et al. |
| 2011/0058175 A1 | 3/2011 | Suehira |

FOREIGN PATENT DOCUMENTS

| JP | 11-325849 A | 11/1999 |
| JP | 2002-139421 A | 5/2002 |
| JP | 2007-24677 A | 2/2007 |
| JP | 2008-203246 A | 9/2008 |
| JP | 2008-237724 A | 10/2008 |
| JP | 2009-294205 A | 12/2009 |
| JP | 2010-38910 A | 2/2010 |
| WO | 2009-136659 A1 | 11/2009 |

OTHER PUBLICATIONS

International Search Report for PCT/JP2010/002301; May 18, 2010.

* cited by examiner

*Primary Examiner* — Michael A Lyons
*Assistant Examiner* — Shawn Decenzo
(74) *Attorney, Agent, or Firm* — Pearne & Gordon LLP

(57) ABSTRACT

An optical image measurement device comprises: a light amount adjustment part that adjusts the light amount of a laser beam generated by a low coherence light source 201; and a photodiode 105 placed outside the light path of the laser beam irradiated on an eye E and capable of measuring the light amount, wherein the laser beam is input to the photodiode 105 by changing the direction of a galvanomirror 170B; the photodiode 105 measures the light amount of the input laser beam; and the light amount adjustment part previously stores a specified range of light amount and adjust the light amount of the laser beam generated by the low coherence light source 201 such that the light amount measured by the photodiode 105 falls within the specified range.

7 Claims, 3 Drawing Sheets

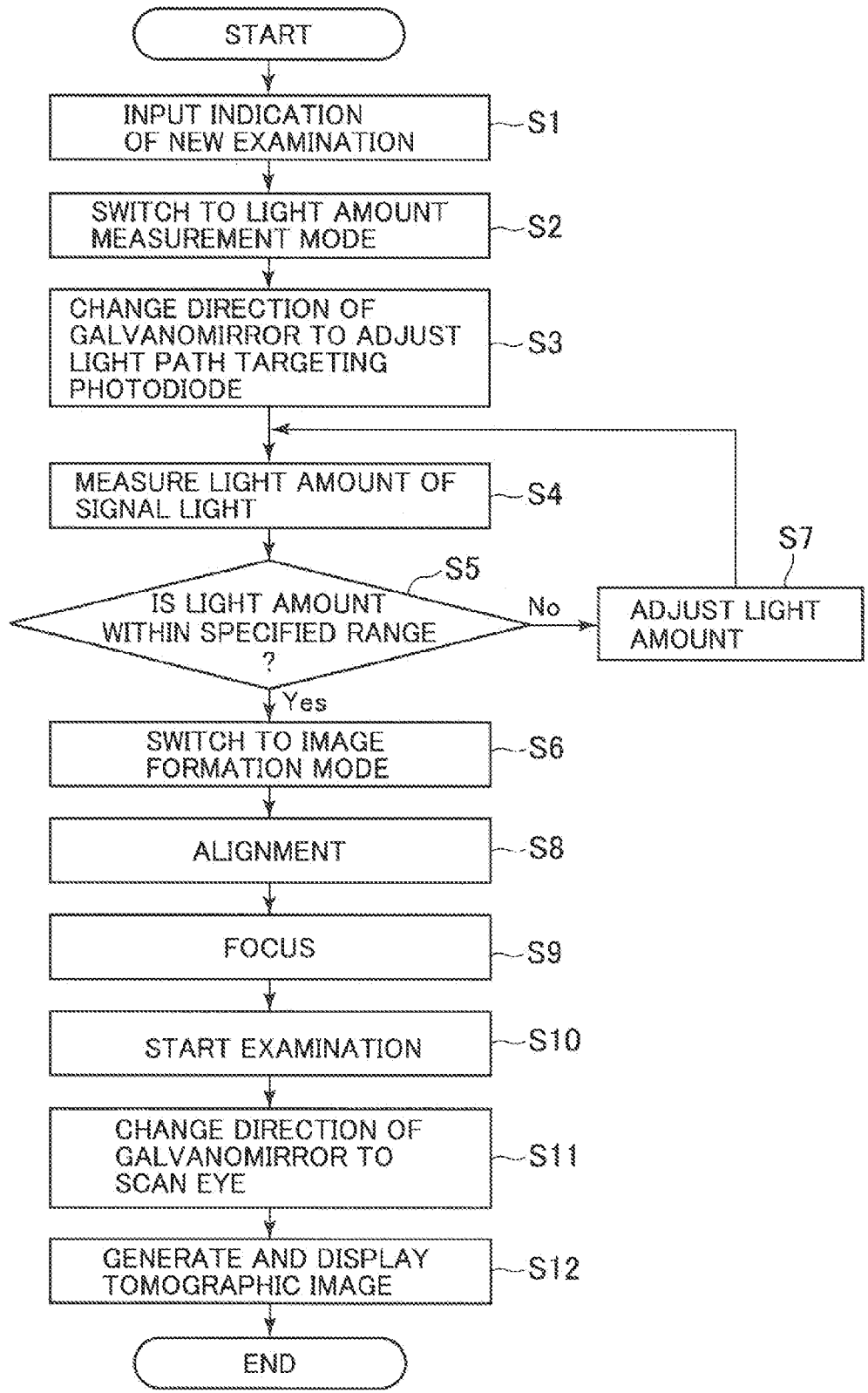

OPTICAL IMAGE MEASUREMENT DEVICE

FIELD OF THE INVENTION

The present invention relates to an optical image measurement device configured to scan a measured object with laser light and to form an image of the measured object using its reflected light.

BACKGROUND

In recent years, an optical image measuring technique of scanning a measured object with light beam from a laser light source etc. and forming images that show the surface morphology and internal morphology of measured objects has attracted attention. Unlike an X-ray CT apparatus, the optical image measuring technique is noninvasive to human bodies, and is therefore expected to be utilized particularly in the medical field.

As examples of such an optical image measurement device, there are an OCT (Optical Coherence Tomography) device and a scanning laser ophthalmoscope (SLO) used in ophthalmology. The SLO is a device that projects laser light into an eyeball with high speed scan, detects a reflected light from a fundus oculi by a high sensitive light detection element, and forms an image. Below, the OCT device is particularly described as an example of the optical image measurement device.

Japanese Unexamined Patent Application Publication No. Hei 11-325849 discloses an example of the optical image measuring technique. This device has such a configuration that: a measuring arm scans an object by a rotary deflection mirror (a galvanomirror); a reference arm is provided with a reference mirror; and an interferometer is mounted at the outlet to analyze, by a spectrometer, the intensity of an interference light of light fluxes from the measurement arm and the reference arm; the reference arm is provided with a device that gradually changes the light flux phase of the reference light by discontinuous values.

The optical image measurement device in Japanese Unexamined Patent Application Publication No. Hei 11-325849 uses a technique of so-called "Fourier Domain OCT (Optical Coherence Tomography)." That is to say, the device radiates a low-coherence light beam to a measured object, acquires the spectral intensity distribution of interference light of the reflected light and the reference light, and executes Fourier transform, thereby imaging the morphology in the depth direction (the z-direction) of the measured object.

Furthermore, the optical image measurement device described in Japanese Unexamined Patent Application Publication No. Hei 11-325849 is provided with a galvanomirror that scans with a light beam (a signal light), and is thereby configured to form an image of a desired measurement target region of the measured object. Because this device is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Japanese Unexamined Patent Application Publication No. 2002-139421 discloses a technique of scanning with a signal light in the scanning direction (the x-direction) and the vertical direction (the y-direction that is perpendicular to both the x-direction and the z-direction) to form a plurality of two-dimensional tomographic images in the scanning direction (the x-direction), and acquiring and imaging three-dimensional tomographic information of a measured range based on the tomographic images. As the three-dimensional imaging, for example, a method of arranging and displaying a plurality of tomographic images in the vertical direction (the y-direction) (referred to as stack data or the like), and a method of executing a rendering process on a plurality of tomographic images to form a three-dimensional image are considered.

Japanese Unexamined Patent Application Publication No. 2007-24677 describes, as an example of other types of optical image measurement devices, an optical image measurement device that images the morphology of a measured object by scanning the measured object with light of various wavelengths, acquiring the spectral intensity distribution based on an interference light obtained by superposing the reflected lights of the light of the respective wavelengths on the reference light, and executing Fourier transform. Such an optical image measurement device is called a Swept Source type or the like.

DISCLOSURE OF THE INVENTION

Problem that the Invention is to Solve

However, as described above, since the optical image measurement device is comprised of various precise optical devices and optical parts including optical fibers, it is easily affected by the usage environment, in particular by the environmental temperature, and is noted for the phenomenon in which the amount of light irradiated to the measured object is reduced. Moreover, degradation of the light source over time (time degradation) also reduces the amount of light irradiated to the measured object. If such a reduction in the amount of light irradiated to the measured object occurs, the signal forming each tomographic image to be formed is lowered, thereby creating a possibly obscured image.

Furthermore, should there be a failure in the light source such as SLD resulting in the light amount from the laser beam irradiated on the measured object becoming higher than necessary, an intense laser beam is irradiated on the measured object. When an intense laser beam is irradiated in this way, if the measured object is an eye (an eye as an measured object is hereinafter referred to as an "eye"), there is also a risk of damaging this eye.

With regard to this point, in conventional optical image measurement devices, when measuring the light amount of the laser beam irradiated on the measured object, the light amount of the laser beam irradiated on the measured object has been measured by preparing equipment for measuring the light amount and arranging this measurement equipment at the position of the measured object. However, with such a method, every time measurement of the light amount of the laser beam irradiated on the measured object is attempted, equipment for measuring the light amount has to be prepared, complicating the operator's tasks in the measurement of the light amount of the laser beam irradiated on the measured object and the adjustment of the light amount. Moreover, since the measurement of the light amount of the laser beam irradiated on the measured object is not easily performed, there has been a risk of mistakenly irradiating an intense laser beam on the measured object.

The present invention is devised taking such backgrounds into consideration, with the object of the invention consisting of providing an optical image measurement device capable of easily measuring the light amount of a laser beam irradiated on an measured object using a light amount measurement device arranged within the optical image measurement device. Moreover, the object of the invention is to provide an optical image measurement device with a high safety level, particularly in the medical field.

Means for Solving the Problem

In order to achieve the above object, the optical image measurement device according to claim 1 comprises: a light source that generates a laser beam; a light amount adjustment part that adjusts said light amount of the laser beam generated by said light source; a scanning part that scans said laser beam on a measured object by changing the irradiation position of said laser beam on said measured object by changing the direction of a galvanomirror; a detection part that detects said laser beam reflected by said measured object; an image formation part that forms an image of said measured object based on the detection result obtained by said detection part; a light amount measuring part that is placed outside the light path of said laser beam irradiated on said measured object and is capable of measuring the light amount; and a mode switching part that alternatively switches between two modes: an image formation mode for forming an image of said measured object and a light amount measurement mode for measuring the light amount of said laser beam; characterized in that: when the mode is switched to said light amount measurement mode by said mode switching part, said scanning part changes the direction of said galvanomirror to input said laser beam to said light amount measuring part; said light amount measuring part measures the light amount of said input laser beam; and said light amount adjustment part previously stores a specified light amount range, and adjusts the light amount of the laser beam generated by said light source such that the light amount measured by the said light amount measuring part falls within said specified range.

The invention according to claim 2 is the optical image measurement device according to claim 1, characterized in that said light amount adjustment part previously stores the upper and lower limits of the light amount as said specified range and compares the light amount measured by said light amount measuring part with each of said upper limit and said lower limit, and when said measured light amount is above said upper limit, then reduces the light amount of the laser beam generated by said light source, and when said measured light amount is below said lower limit, then increases the light amount of the laser beam generated by said light source.

The invention according to claim 3 is the optical image measurement device according to claim 1, characterized in that: said light amount adjustment part previously stores the upper limit of the light amount of said laser beam as said specified range and compares the light amount measured by said light amount measuring part with said upper limit; and further comprising an alarm part that informs an alarm when said measured light amount is above said upper limit.

The invention according to claim 4 is the optical image measurement device according to claim 1, characterized in that: said light amount adjustment part previously stores the upper limit of the light amount of said laser beam as said specified range and compares the light amount measured by said light amount measuring part with said upper limit; and further comprising an irradiation prevention part that prevents the irradiation of said laser beam on said measured object when said measured light amount is above said upper limit.

The invention according to claim 5 is the optical image measurement device according to claim 1, further comprising a maximum brightness acquisition part that acquires the maximum brightness of the image formed by said image formation part, characterized in that said light amount adjustment part previously stores the maximum brightness threshold for the lower limit of the maximum brightness of the image as said specified range and compares the maximum brightness acquired by said maximum brightness acquisition part with said maximum brightness threshold, and when said maximum brightness is below said maximum brightness threshold, then adjusts the light amount of the laser beam generated by said light source to fall within said specified range.

The invention according to claim 6 is the optical image measurement device according to claim 1, further comprising an operation part that is used for initiating the irradiation of said laser beam on said measured object, characterized in that: said mode switching part switches, corresponding to the operation of said operation part, the mode to said light amount measurement mode to allow said light amount measuring part to measure the light amount of said laser beam, and subsequently, if the light amount initially measured by said light amount measuring part falls within said specified range, or if the light amount of said laser beam is adjusted by said light amount adjustment part, then switches the mode to said image formation mode to initiate the forming of the image of said measured object.

The optical image measurement device according to claim 7 comprises: a light source that generates a low coherence light; a light amount adjustment part that adjusts the light amount of said low coherence light generated by said light source; an interference light detection part that divides said low coherence light into signal light and reference light, scans said signal light on a measured object by changing the irradiation position of said signal light on said measured object by changing the direction of a galvanomirror, superposes said signal light reflected by said measured object and said reference light travelling through the reference light path to generate interference light, and detects said interference light; a tomographic image formation part that forms a tomographic image of said measured object based on the detection result obtained by said interference light detection part; a light amount measuring part that is placed outside the light path of said signal light irradiated on said measured object and is capable of measuring the light amount; and a mode switching part that alternatively switches between two modes: an image formation mode for forming an image of said measured object to be measured and a light amount measurement mode for measuring the light amount of said signal light; characterized in that: when the mode is switched to said light amount measurement mode by said mode switching part, said interference light detection part changes the direction of said galvanomirror to input said signal light to said light amount measuring part; said light amount measuring part measures the light amount of said input signal light; and said light amount adjustment part previously stores specified range of light amount, and adjusts the light amount of the low coherence light generated by said light source such that the light amount measured by said light amount measuring part falls within said specified range.

Effect of the Invention

According to the invention, by changing the course of the laser beam targeting the measured object, the light amount of the laser beam targeting the measured object can be measured by the light amount measuring part arranged within the device. Consequently, the light amount of the laser beam targeting the measured object can be easily measured without separately preparing a light amount measurement device for measuring the light amount, thereby making the task less complicated.

In addition, according to the invention, based on the light amount measured by the light amount measuring part arranged within the device, the light amount of the laser beam targeting the measured object can be automatically adjusted. Consequently, the task of adjusting the light amount of the laser beam targeting the measured object can be made less complicated, thereby enabling easy handling of time degradation and change due to the environment of the light source.

Moreover, according to the invention, it is possible to be notified by an alarm when the light amount of the laser beam targeting the measured object exceeds the adjustable value. Consequently, the operator can easily understand when a situation arises in which the light amount of the laser beam cannot be adjusted, thereby improving the safety level of the device.

Furthermore, according to the invention, it is possible to prevent irradiation of the laser beam on the measured object when the light amount of the laser beam targeting the measured object exceeds the adjustable value. Consequently, irradiation of the laser beam on the measured object is not conducted in the situation in which the light amount of the laser beam cannot be adjusted, thereby improving the safety level of the device.

BRIEF DESCRIPTION OF THE DRAWINGS

FIG. 3 is a flow chart showing an example of an operation of the embodiment of the optical image measurement device according to the present invention.

DETAILED DESCRIPTION

First Embodiment

An optical image measurement device according to the present invention is a device configured to scan a measured object with laser light and to form an image of the measured object using its reflected light, and an SLO and an OCT are the examples.

In the following description, an example of an embodiment of an optical image measurement device according to the present invention will be described in detail with reference to the drawings. In this embodiment, a device that is used in the ophthalmologic field to acquire an OCT image of a living eye will be described. A living eye is moving at all times due to eye movement such as involuntary eye movement, heartbeats, and so on. Similar actions and effects can be obtained by a similar configuration also at the time of acquisition of an OCT image of a measured object other than a living eye. Moreover, other types of optical image measurement devices such as an SLO are able to provide similar actions and effects by a similar configuration.

In this embodiment, a configuration to which a Fourier-Domain-type OCT technique is applied will be described in detail. In a case that another configuration is applied, application of a similar configuration to that of this embodiment makes it possible to obtain similar actions and effects. For example, it is possible to apply the configuration according to this embodiment to any type of OCT device that scans with a signal light and executes measurement as in the Swept Source type.

[Configuration]

Figure 1:
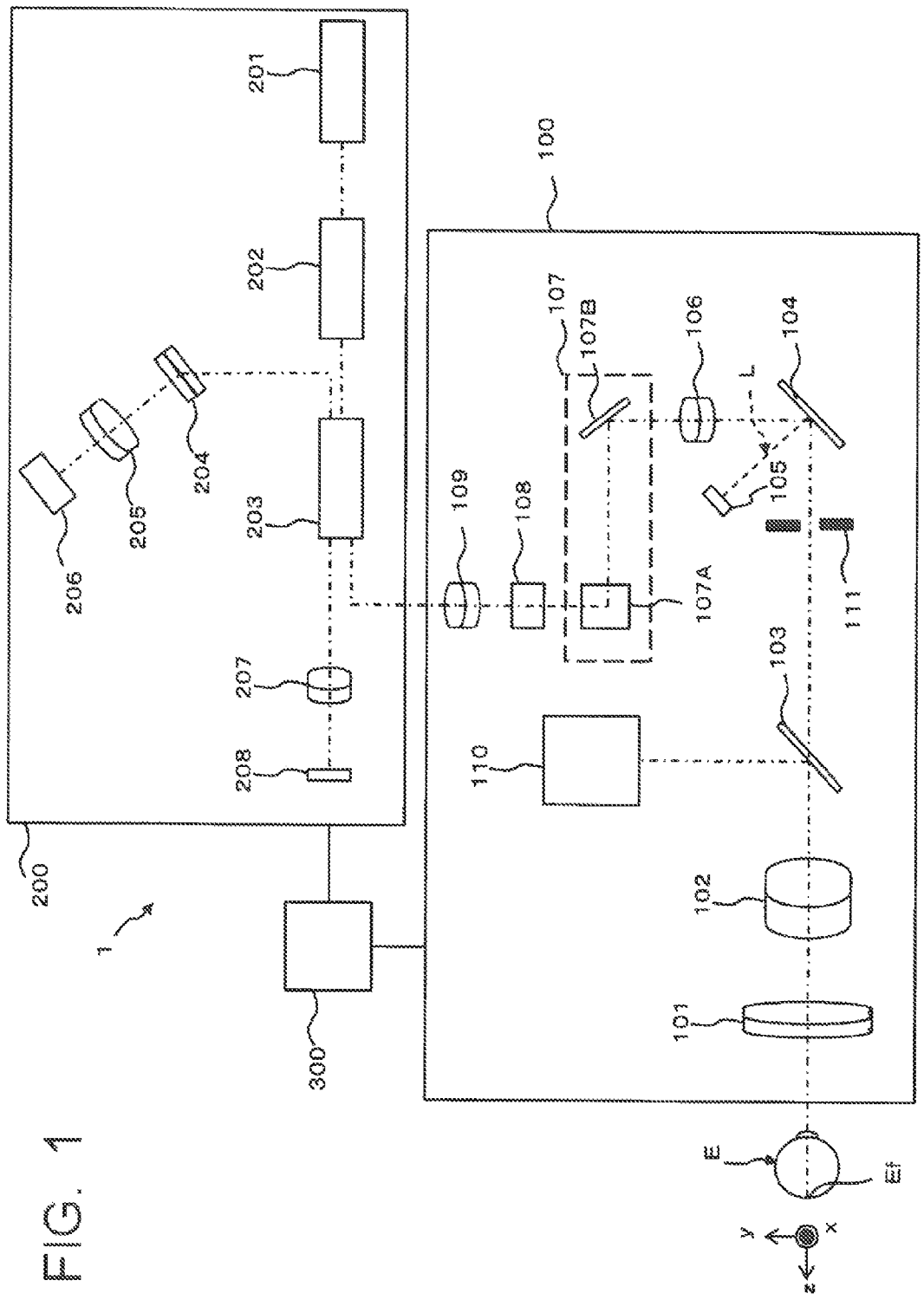
FIG. 1 is a schematic constitution diagram showing an example of an entire configuration of an embodiment of an optical image measurement device according to the present invention.

An optical image measurement device 1, as shown in FIG. 1, includes a retinal camera unit 100, an OCT unit 200, and an arithmetic and control unit 300. These components are arranged separately in several cases, or arranged together in a case. The retinal camera unit 100 has almost the same optical system as a conventional retinal camera. A retinal camera is a device that photographs the fundus oculi. Moreover, a retinal camera is utilized for photographing the morphology of fundus oculi blood vessels. The OCT unit 200 houses an optical system for acquiring an OCT image of the fundus oculi Ef. The arithmetic and control unit 300 is provided with a computer that executes various arithmetic processes, control processes, and so on.

The retinal camera unit 100 and the OCT unit 200 are optically connected via a fiber cable. The arithmetic and control unit 300 is connected to both the retinal camera unit 100 and the OCT unit 200 via a communication line for transmitting electrical signals. Moreover, the optical image measurement device 1 has two operational modes: a light amount measurement mode and an image formation mode. Here, the light amount measurement mode is a mode for measuring the light amount of the laser beam output from the light source. Further, the image formation mode is a mode for forming a tomographic image of the measured object.

[Retinal Camera Unit]

The retinal camera unit 100 has an optical system for forming a two-dimensional image showing the morphology of the fundus oculi surface. A two-dimensional image of the fundus oculi surface includes a color image and a monochrome image obtained by photographing the fundus oculi surface and a fluorescent image (a fluorescein angiography image, an indocyanine green fluorescent image, and so on).

The retinal camera unit 100, as is the case with conventional retinal cameras, is provided with various user interfaces. Examples of the user interfaces include an operation panel, a control lever (joystick), an imaging switch, a focus handle, a display, etc. A chin rest and the forehead placement for retaining the face of the subject are provided at the position of the subject side (the front surface) of the retinal camera unit 100.

The retinal camera unit 100 is provided with an observation and imaging optical system 110 including an illumination optical system and imaging optical system as in conventional fundus cameras. The structure of this observation and imaging optical system 110 is the same as the structure in conventional retinal camera units. Specifically, the observation and imaging optical system 110 has a light source that irradiates illumination light at a wavelength of about 400 nm to 800 nm, for example, and an imaging device (neither are shown).

The illumination light output from the light source passes through various optical elements included in the observation and imaging optical system 110 and arrives at a dichroic mirror 103. Moreover, this illumination light is reflected by the dichroic mirror 103 and condensed by passing through the condenser lens system 102. The condensed illumination light enters an eye E through an objective lens 101 and illuminates the fundus oculi Ef.

The dichroic mirror 103 reflects the fundus oculi reflected light (having a wavelength included in the range from about 400 to 800 nm) of the illumination light coming from the observation and imaging optical system 110. Moreover, the dichroic mirror 103 transmits a signal light (having a wavelength included in the range from about 800 to 900 nm, for example) coming from the OCT unit 200.

An imaging device included in the retinal camera unit 100 detects a fundus oculi reflected light of the illumination light and outputs video signals.

Moreover, the retinal camera unit 100 is provided with a photodiode 105. This photodiode 105 detects light and performs photoelectric conversion, measuring the light amount of the detected light based on the electric current or voltage of the electric signal. This photodiode 105 corresponds to the "light amount measuring part" in the present invention. However, this light amount measuring part is not limited to a photodiode, and other mechanisms for measuring the light amount may be used.

Subsequently, the photodiode 105 is placed at a position outside the light path of a signal light targeting the eye E. Specifically, it is sufficient if the photodiode 105 is placed outside a diaphragm hole that passes light in a diaphragm 111 placed at a position conjugated with the fundus oculi Ef in the light path, and at a position in which the light targeting the photodiode 105 is not irradiated to the diaphragm hole. Moreover, when the photodiode 105 is placed at a position conjugated with the diaphragm 111, it is not necessary to separately add an optical system for measuring the light amount, enabling the light amount measurement system to be more easily constituted.

The retinal camera unit 100 is provided with a scan unit 107. The scan unit 107 scans a target position on the fundus oculi Ef with the signal light output from the OCT unit 200.

In the image formation mode, the scan unit 107 scans the signal light in the xy-plane shown in FIG. 1. To this end, the scan unit 107 is provided with, for example, a galvanomirror 107A for scanning in the x-direction and a galvanomirror 107B for scanning in the y-direction. The direction of the galvanomirrors 107A and 107B is changed by applying a voltage. Subsequently, the galvanomirrors 107A and 107B are placed in a predetermined reference position at a voltage of 0 V. This reference position is preset such that, for example, the light path of the signal light passes through the center of the diaphragm hole. Scanning of the eye E in the y-direction is performed within a range of approximately ±6.5 mm. Therefore, when performing scanning of the eye E, in the present embodiment, the direction of the galvanomirror 107B (in the y-direction) is changed by approximately 3.5 degrees. The diaphragm hole of the diaphragm 111 is of a size such that the signal light, which has been changed in direction by 3.5 degrees by the galvanomirror 107B relative to the reference position, can pass through. Moreover, in the present embodiment, the maximum movable angle of the galvanomirror 107B is about 20 degrees.

Moreover, in the light amount measurement mode, the scan unit 107 changes the direction of the galvanomirror 107B in order to irradiate the signal light onto the photodiode 105. The light path of this signal light targeting the photodiode 105 is the light path L represented by the dotted line in FIG. 1. In this case, the galvanomirror 107A is directed to the reference position. In the present embodiment, by changing the direction of the galvanomirror 107B from the reference position by 5.5 degrees, the signal light is irradiated on the photodiode 105 through the light path L. Here, as described above, since the diaphragm 111 is configured so as to allow signal light to pass through in the situation in which the direction of the galvanomirror 107B changed from the reference position by 3.5 degrees, the light path L of the signal light with the direction of the galvanomirror 107B changed by 5.5 degrees does not pass through the diaphragm 111. Therefore, when the signal light passes through the light path L through which the signal light is irradiated on the photodiode 105, the signal light is not irradiated on the eye E.

Meanwhile, in the present embodiment, the light path is moved in the y-direction by changing the direction of the galvanomirror 107B to irradiate the light on the photodiode 105; however, in practice, the position of the photodiode 105 may be any position if it is a position in which the signal light irradiated on the photodiode is not irradiated on the eye E. For example, in order to irradiate the signal light on the photodiode 105, the configuration may be such that the photodiode 105 is placed in the position targeted by the signal light when the direction of the galvanomirror 107A is changed; furthermore, the configuration may be such that the photodiode 105 is placed in the position targeted by the signal light when the direction of both galvanomirrors 107A and 107B is changed.

[OCT Unit]

A configuration of the OCT unit 200 will be described. The OCT unit 200 has an optical system similar to that of a conventional Fourier-Domain-type optical image measurement device. That is to say, the OCT unit 200 has: an optical system that splits a low-coherence light into a reference light and a signal light, makes the signal light reflected by the fundus oculi Ef of the eye E and the reference light propagated through a reference object interfere with each other to generate an interference light, and detects the spectral components of this interference light to generate a detection signal. This detection signal is transmitted to the arithmetic and control unit 300.

A low-coherence light source 201 is a broadband light source that outputs a broadband low-coherence light. As this broadband light source, for example, a super luminescent diode (SLD), a light emitting diode (LED) and the like can be used. This low coherence light corresponds to the "laser beam" in the present invention, with the low coherence light source 201 corresponding to the "light source" in the present invention. By increasing or decreasing the light amount of the low coherence light output from the low coherence light source 201, the light amount of the signal light is correspondingly increased or decreased. That is, when the light amount of the signal light is increased, the intensity of the light irradiated on the eye E is increased. In addition, it is dangerous if the light amount of the signal light irradiated on the eye E exceeds 700 µW. That is, the light amount of the signal light irradiated on the eye E is preferably 700 µW or less. Here, the light amount usually refers to the amount of the light irradiated for a specified time; however, the light amount is commonly used to indicate the intensity of the light, so the light amount is similarly used herein to indicate the intensity of the light.

For example, the low-coherence light includes a light of a wavelength in the near-infrared region and has a temporal coherence length of about tens of micrometers. The low-coherence light includes a longer wavelength than the illumination light of the retinal camera unit 100 (a wavelength of about 400-800 nm), for example, a wavelength in the range from about 800 to 900 nm.

The low-coherence light output from the low-coherence light source 201 is led to an isolator 202 through an optical fiber.

The isolator 202 serves to prevent low coherence light from returning to the low coherence light source 201, thus protecting the low coherence light source 201.

The low-coherence light output from the isolator 202 is led to an optical coupler 203 through an optical fiber. The optical coupler 203 splits the low-coherence light into the reference light and the signal light.

The optical coupler 203 has functions of both a part that splits the low-coherence light into the reference light and the signal light (a splitter) and a part that superposes lights (a coupler), but will be idiomatically referred to as an "optical coupler" herein.

The reference light generated by the optical coupler 203 is led by an optical fiber, and is emitted from the end face of the fiber. Furthermore, the reference light is condensed by a condenser lens system 207, and reflected by a reference mirror 208.

The reference light reflected by the reference mirror 208 is again propagated through the condenser lens system 207, and led to the optical coupler 203 through the optical fiber.

The reference mirror 208 and the condenser lens system 207 are moved in the travelling direction of the reference light by the predefined driving mechanism. Accordingly, in response to the axial length of the subject's eye E and the working distance (the distance between the objective lens 113 and the subject's eye E), the optical path length of the reference light can be assured.

On the other hand, the signal light generated by the optical coupler 203 is guided by the optical fiber and introduced to the retinal camera unit 100. Moreover, when the optical image measurement device 1 is in the image formation mode, the signal light is irradiated on the fundus oculi Ef through the condenser lens system 109, deflection mirror 108, scan unit 107, condenser lens system 106, deflection mirror 104, diaphragm 111, dichroic mirror 103, condenser lens system 102, and objective lens 101. Further, when the optical image measurement device 1 is in the light amount measurement mode, the signal light is irradiated on the photodiode 105 through the condenser lens system 109, deflection mirror 108, scan unit 107, condenser lens system 106, and deflection mirror 104.

The signal light having entered the eye E forms an image and reflected at fundus oculi Ef. At this moment, the signal light is not only reflected at the surfaces of the fundus oculi Ef but also scattered at a refractive index boundary of the deep part of fundus oculi Ef. Therefore, the signal light propagated through the fundus oculi Ef includes information that reflects the morphology of the surface of the fundus oculi Ef, and information that reflects a state of back scatter at the refractive index boundary of the deep tissues of the fundus oculi Ef. This light may be simply called as a fundus oculi reflected light of the signal light.

The fundus oculi reflected light of the signal light is guided reversely on the same path as the signal light travelling to the eye E, thereby it enters the OCT unit 200 and returns to the optical coupler 203.

The optical coupler 203 makes the signal light having returned through the fundus oculi Ef interfere with the reference light having returned after reflected by the reference mirror 208 to generate the interference light.

The interference light is led to a diffraction grating 204 through an optical fiber. The diffraction grating 204 may be either a transmission-type or a reflection-type. The interference light is divided into spectra by the diffraction grating 204 (spectral resolution).

The divided interference light is formed into an image on the image pick-up face of the line CCD 206 (simply referred to as "CCD 206") by the condenser lens system 205. The CCD 206 detects the respective spectral components of the divided interference light and converts the components into electric charges. The CCD 206 accumulates these electric charges and generates detection signals. Furthermore, the CCD 206 transmits these detection signals to the arithmetic and control unit 300. Moreover, it is also possible to use another photodetecting device (a line sensor or an area sensor) such as a CMOS, instead of the CCD 206.

The "scanning part" according to the present invention is configured to include the scan unit 107.

Moreover, a "detection part" according to the present invention is configured to include, for example, the optical coupler 203, optical members on the light path of the interference light (i.e. an optical member placed in between the optical coupler 203 and the CCD 206) and optical members on the light path of the reference light (i.e. an optical member placed between the optical coupler 203 and the reference mirror 208), and particularly includes an interferometer comprising the optical coupler 203, the optical fibers and the reference mirror 208, and furthermore, it has the CCD 206.

Moreover, the combination of the part corresponding to this "scanning part" and a part corresponding to the "detection part" corresponds to an "interference light detection part".

Although a Michelson-type interferometer is employed in this embodiment, it is possible to employ any type of interferometer such as a Mach-Zehnder-type as necessary.

[Arithmetic and Control Unit]

A configuration of the arithmetic and control unit 300 will be described. The arithmetic and control unit 300 analyzes the detection signals inputted from the CCD 206, and forms an OCT image of the eye E. An arithmetic process for forming an OCT image is like that of a conventional Fourier-Domain-type OCT device.

Further, the arithmetic and control unit 300 controls each part of the retinal camera unit 100 and the OCT unit 200.

As control of the retinal camera unit 100, the arithmetic and control unit 300 executes control of output of the illumination light, control of the aperture value of the diaphragm 111 and so on. Furthermore, the arithmetic and control unit 300 controls the galvanomirrors 107A and 107B to scan with the signal light.

Further, as control of the OCT unit 200, the arithmetic and control unit 300 executes: control of output of the low-coherence light by the low-coherence light source 201; control of movement of the reference mirror 208; control of an accumulation time for electric charge, the timing for electric charge accumulation and the timing for signal transmission by the CCD 206; and so on.

The arithmetic and control unit 300 includes a microprocessor, a RAM, a ROM, a hard disk drive, a keyboard, a mouse, a display, a communication interface, and so on, as in conventional computers. The hard disk drive stores a computer program for controlling the optical image measurement device 1. Moreover, the arithmetic and control unit 300 may be provided with a circuit board dedicated for forming OCT images based on detection signals from the CCD 206.

[Control System]

Figure 2:
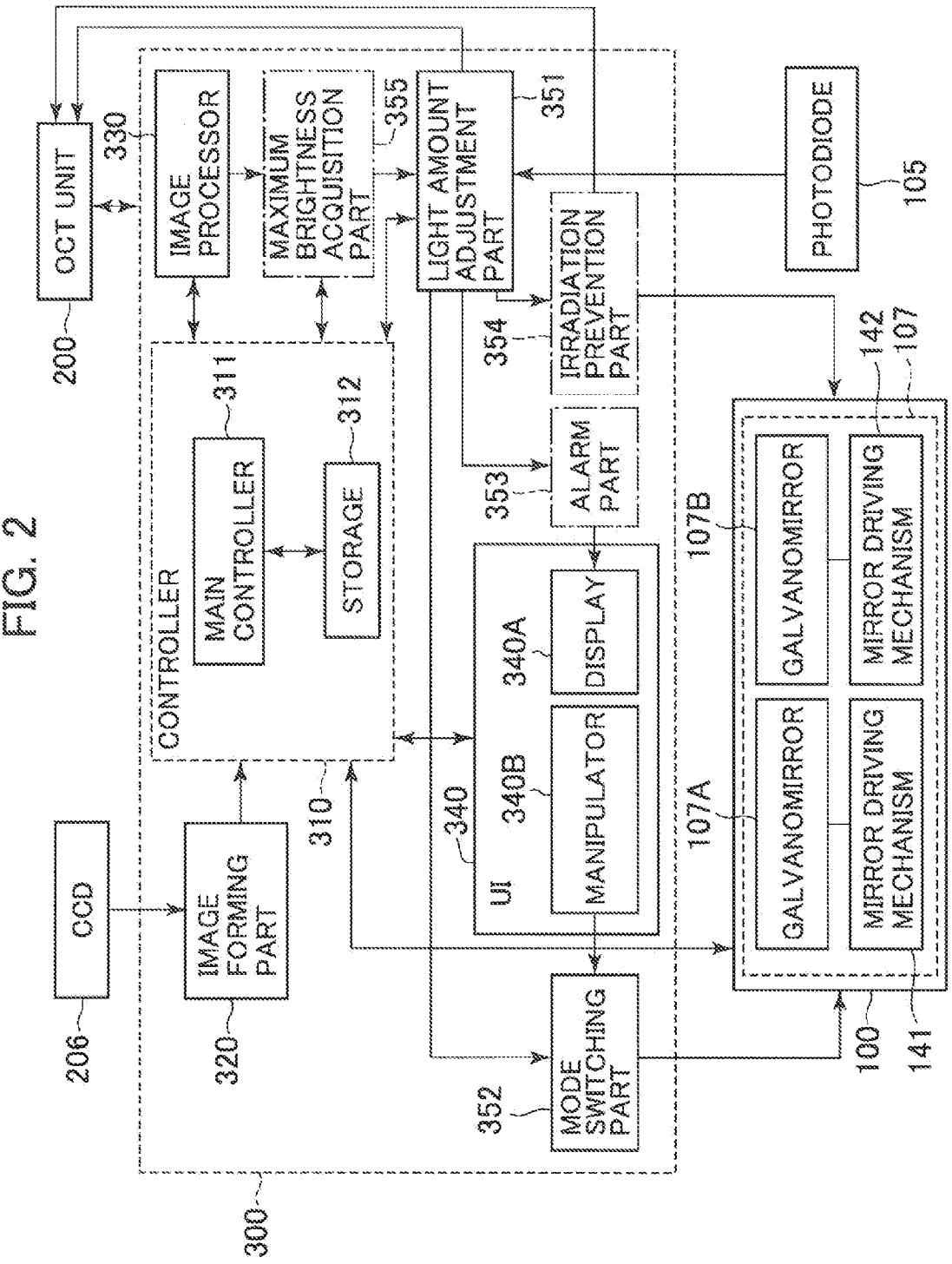
FIG. 2 is a schematic diagram showing an example of a configuration of a control system of the embodiment of the optical image measurement device according to the present invention.

A configuration of a control system of the optical image measurement device 1 will be described with reference to FIG. 2. In FIG. 2, the CCD 206 and the OCT unit 200 are separately described. However, in practice, as explained above, the CCD 206 is provided in the OCT unit 200.

(Controller)

The control system of the optical image measurement device 1 has a configuration centered on a controller 310. The controller 310 includes, for example, the aforementioned microprocessor, RAM, ROM, hard disk drive, and communication interface.

The controller 310 is provided with a main controller 311 and a storage 312. The main controller 311 controls each part of the retinal camera unit 100, the OCT unit 200 and the arithmetic and control unit 300.

(Main Controller)

The main controller 311 controls the mirror driving mechanisms 141 and 142 to control the direction (angle) of the galvanomirrors 107A and 107B, thereby scanning of the signal light on the fundus oculi Ef.

(Storage)

The storage 312 stores various kinds of data. The data stored in the storage 312 is, for example, image data of OCT images, image data of fundus oculi images, and eye information. The eye information includes various information on the eye, for example, information on a subject such as a patient ID and a name, information on identification of left eye or right eye, and diagnostic result and examination result of the eye. The main controller 311 executes a process of writing data into the storage 312, and a process of reading out the data from the storage 312.

Moreover, the storage 312 stores the angles of the galvanomirrors 107A and 107B, allowing the signal light to enter the photodiode 105. In addition, the storage 312 stores, as a specified light amount range, the upper limit threshold and the lower limit threshold of the light amount. In the present embodiment, the storage 312 stores 700 µW as the upper limit threshold and 400 µW as the lower limit threshold. However, other values may be set for these thresholds, preferably setting values corresponding to the operation. For example, in order to further enhance the safety of the eye E, lower values such as 600 µW may be set for the upper limit threshold; whereas, in order to further improve the image quality, higher values such as 500 µW may be set for the lower limit threshold. This upper limit threshold corresponds to the "upper limit" in the present invention, with the lower limit threshold corresponding to the "lower limit" in the present invention.

Moreover, a computer program for executing an action (flow chart), which is described below, is stored in the storage 312. The main controller 311 operates based on the data and the computer program.

(Image Forming Part)

An image forming part 320 forms image data of a tomographic image of the fundus oculi Ef based on the detection signals from the CCD 206. Like the conventional Fourier-Domain OCT technique, this image data forming process includes processes such as noise elimination (noise reduction), filtering, and FFT (Fast Fourier Transform).

The image forming part 320 is configured to include, for example, the aforementioned circuit board and communication interface. In this specification, "image data" may be identified with an "image" presented based on the image data.

(Image Processor)

An image processor 330 executes various image processing and analysis on fundus oculi images (photographs of a retinal surface) obtained by the retinal camera unit 100 and images formed by the image forming part 320. For example, the image processor 330 executes various correction processes such as luminance correction and dispersion correction of images.

Further, the image processor 330 executes, for example, an interpolation process of interpolating pixels between tomographic images formed by the image forming part 320, thereby forming image data of a three-dimensional image of the fundus oculi Ef.

The image processor 330 having the aforementioned configuration includes, for example, a microprocessor, RAM, ROM, hard disk drive and so on. Moreover, the image processor 330 may include a dedicated circuit board and the like that executes a predetermined image processing and analysis processing.

The quality of the tomographic image formed by the above image forming part 320 and image-processing part 330 becomes degraded when the light amount of the signal light irradiated on the eye E is less than 400 µW, resulting in an image difficult to use for diagnosis. Consequently, the light amount of the signal light irradiated on the eye E is preferably 400 µW or more.

The formation of the tomographic image described above is conducted when the optical image measurement device 1 is in the image formation mode.

Meanwhile, the image forming part 320 (and the image-processing part 330) serves as an example of a "tomographic image formation part" according to the present invention.

(Light Amount Adjustment Part)

When the optical image measurement device 1 is in the light amount measurement mode, the light amount adjustment part 351 performs the following operation. The light amount adjustment part 351 receives an input of the measurement result of the light amount of the signal light measured by the photodiode 105. The light amount adjustment part 351 then compares the upper limit threshold (700 µW) and the lower limit threshold (400 µW) stored in the storage 312 with the measurement result of the light amount of the signal light. Then, if the light amount of the signal light measured is greater than the upper limit threshold, the light amount adjustment part 351 controls the low coherence light source 201 so as to reduce the light amount of the low coherence light. Moreover, if the measurement result of the light amount of the signal light is below the upper limit threshold, the light amount adjustment part 351 controls the low coherence light source 201 so as to increase the light amount of the low coherence light. The combination of the light amount adjustment part 351 and the storage 312 corresponds to the "light amount adjustment part" in the present invention.

(Mode Switching Part)

Upon receipt of the input from the operating part 340B indicating that a new examination is to be conducted, the mode switching part 352 switches the operational mode of the retinal camera unit 100 to the light amount measurement mode. Then, if it is determined by the light amount adjustment part 351 that the measurement result of the light amount of the signal light by the photodiode 105 is equal to or less than the upper limit threshold and equal to or greater than the lower limit threshold, the mode switching part 352 switches the operational mode of the optical image measurement device 1 to the image formation mode. On the other hand, if it is determined by the light amount adjustment part 351 that the measurement result of the light amount of the signal light is greater than the upper limit threshold or is below the lower limit threshold, the light amount adjustment part 351 adjusts the light amount. Then, if it is determined by the light amount adjustment part 351 that the light amount of the signal light measured at the photodiode 105 is equal to or less than the upper limit threshold and equal to or greater than the lower limit threshold, the mode switching part 352 switches the operational mode of the optical image measurement device 1 to the image formation mode.

Meanwhile, in the present embodiment, in order to improve the safety and image quality of the tomographic images, the optical image measurement device 1 is operated in the light amount measurement mode for every new examination in order to measure and adjust the light amount of the signal light targeting the eye E; however, the timing of the operation in this light amount measurement mode is preferably implemented taking into consideration the safety and image quality of the tomographic image required for each optical image measurement device 1. For example, the configuration may be such that the optical image measurement device 1 is operated in the light amount measurement mode upon turning on the optical image measurement device 1.

Moreover, as other examples of timing of the mode switching to the light amount measurement mode, a timer is provided in the mode switching part 352, and in addition, the mode switching part 352 previously stores a specified time (for example, 3 hours). Subsequently, the mode switching part 352 may be configured to count the operating time of the optical image measurement device 1 using this timer and, every time this operating time passes the specified time, switch the operational mode of the optical image measurement device 1 to the light amount measurement mode to automatically perform the light amount measurement. Here, when the examination is in fact being conducted (when operating in the image formation mode) at the time when the specified time has elapsed, the mode is switched to the light amount measurement mode once this examination is completed in order to carry out the light amount measurement.

Moreover, in this case, the timer is provided inside the mode switching part 352; however, the configuration may be such that a time counting part that counts the operating time of the optical image measurement device 1 is separately provided and the time counting part stores the specified time. When the time counting part is separately provided in such a way, it is sufficient if the mode switching part 352 is configured to switch the operational mode of the optical image measurement device 1 to the light amount measurement mode upon receipt of notification from the time counting part indicating that the operating time has passed the specified time.
(Display and Manipulator)

A user interface 340 includes a display 340A and a manipulator 340B. The manipulator 340B is constituted by including input devices and operation devices, such as a keyboard and a mouse. Moreover, various input devices and operation devices that are provided on the housing surface and on the external sections of the optical image measurement device 1 are included in the manipulator 340B.

The display 340A and the manipulator 340B do not need to be composed as separate devices. For example, like a touch panel LCD, a device in which the display 340A and the manipulator 340B are formed in one body can be used.
[Operation]

The operation of the optical image measurement device 1 will be described. The flow chart shown in FIG. 3 represents an example of the usage pattern of the optical image measurement device 1 according to the present embodiment.

S1 to S7 in FIG. 3 are preliminary stages and S8 to S12 are stages for conducting actual examinations. In the FIG. 3, the preliminary stages and the stages for conducting actual examinations are shown continuously for the purpose of illustration; however, there may be a time interval between the preliminary stages and the stages for conducting actual examinations.

First, the operator operates the operating part 340B to enter the input indicating that a new examination is to be conducted (S1).

Upon receipt of the input from the operator indicating that a new examination is to be conducted, the mode switching part 352 switches the operational mode of the optical image measurement device 1 to the light amount measurement mode (S2).

The controller 310 places the galvanomirror 107A in the reference position while changing the direction of the galvanomirror 107B to adjust the light path of the signal light targeting the photodiode 105 (S3). Here, when the galvanomirror 107A has been placed in the reference position as in the case of power-on, it is not necessary to change the direction of the galvanomirror 107A.

Subsequently, a low coherence light is output from the low coherence light source 201 and the signal light is irradiated on the photodiode 105. The photodiode 105 measures the light amount of the irradiated signal light (S4).

Upon receipt of the input of the measurement result of the light amount of the signal light from the photodiode 105, the light amount adjustment part 351 compares the input measurement result with the upper limit threshold and the lower limit threshold stored in the storage 312 (S5). Then, if it is determined by the light amount adjustment part 351 that the measurement result is greater than the upper limit threshold or is below the lower limit threshold (No in S5), the process proceeds to Step 7. On the other hand, if it is determined by the light amount adjustment part 351 that the measurement result is equal to or less than the upper limit threshold and equal to or greater than the lower limit threshold (i.e. within the specified range) (Yes in S5), the process proceeds to Step 6.

When the mode switching part 352 receives notification from the light amount adjustment part 351 indicating that the light amount of the signal light falls within the specified range (Yes in S5), it switches the operational mode of the optical image measurement device 1 to the image formation mode (S6).

In the case of "No" in S5, the light amount adjustment part 351 adjusts the light amount of the low coherence light output from the low coherence light source 201 (S7). After adjusting the light amount, the process returns to Step 4 and measurement of the signal light and comparison between the measurement result and the thresholds are again carried out.

The eye E is placed in the specified measurement position (position facing the objective lens 101), and alignment between the eye E and the device is performed (S8). When alignment is completed, the main controller 311 then focuses on the eye E (S9).

When alignment adjustment and focusing adjustment are completed, the operator operates the operating part 340B in order to request initiation of the examination (S10).

The main controller 311 then controls the low coherence light source 201 and the CCD 206 while simultaneously controlling the mirror driving mechanisms 141 and 142 to change the direction of the galvanomirrors 107A and 107B, thereby scanning the fundus oculi Ef (S11).

Subsequently, the image forming part 320 acquires the detected signals of the fundus oculi components output from the CCD 206 and derives the spectrum intensity distribution based on the detected signals, forming a tomographic image by imaging the morphology of the fundus oculi Ef in the depth direction (Z direction) by performing the Fourier transform of the spectrum intensity distribution of the interference light using the Fourier domain OCT approach (S12).

Actions and Effects

The actions and effects of the optical image measurement device 1 as described above will be described.

The optical image measurement device 1 irradiates the laser beam (signal light) on the photodiode 105 placed outside the light path of the signal light irradiated on the measured object (eye E) by changing the direction of the galvanomirror 170B, and measures the light amount of the laser beam. Moreover, the optical image measurement device 1 is configured so as to automatically adjust the output of the light source such that the measured light amount of the laser beam falls within the specified range.

According to such an optical image measurement device 1, when measuring the light amount of the laser beam targeting the measured object, the light amount of the signal light can be easily measured without preparing other tools for measuring the light amount. Consequently the task of light amount measurement can be made less complicated. Moreover, it is not necessary to use other tools for measuring the light amount in the light amount adjustment as well, further making the task of light amount adjustment of the signal light targeting the measured object less complicated. Consequently, it is possible to easily handle time degradation and changes due to the environment of the light source.

In addition, according to such an optical image measurement device 1, the light amount of the laser beam can be automatically adjusted using the upper limit threshold, thereby ensuring the safety of the eye. Moreover, according to the optical image measurement device 1, the light amount of the laser beam can be automatically adjusted using the lower limit threshold, making it possible to mitigate the disadvantage of having to conduct a reexamination due to a low quality tomographic image being obtained.

MODIFIED EXAMPLE 1

The configuration described above is merely one example for favorably implementing the optical image measurement device according to the present invention. Therefore, it is possible to properly make arbitrary modification within the scope of the present invention.

In the above embodiment, the configuration is such that the light amount is automatically adjusted such that the light amount of the laser beam measured at the photodiode falls within a specified range; however, the configuration may be such that this light amount adjustment is not automatically performed. In this case, the measurement result of the light amount of the laser beam may be displayed to allow the operator to recognize the light amount of the laser beam targeting the measured object.

Also in this modified example, similarly to the above embodiment, the optical image measurement device 1 is operated in the light amount measurement mode at a specified timing. The controller 310 changes the direction of the galvanomirrors 107A and 107B such that the signal light passes through the light path L and is irradiated on the photodiode 105. The photodiode 105 then measures the light amount of the irradiated signal light and the main controller 311 displays the measurement result on the display 340A.

As described above, the optical image measurement device according to the present modified example is configured such that the operator can recognize the light amount of the measured signal light. Consequently, the operator can recognize the light amount of the signal light targeting the eye E and manually adjust the output of the light source based on the measurement result.

As described above, the optical image measurement device according to the present modified example is configured such that the laser beam (signal light) is irradiated on the photodiode placed outside the light path of the laser beam irradiated on the measured object (eye) by changing the direction of the galvanomirror, with the light amount of the laser beam measured by this photodiode and the measurement result displayed on the display.

Even with this configuration, as in the embodiment described above, the operator can recognize the light amount of the laser beam targeting the measured object and easily measure the light amount without preparing other tools for measuring the light amount, thereby making the task less complicated for light amount measurement.

Second Embodiment

The second embodiment of the optical image measurement device according to the invention will be described. This embodiment is configured to, in addition to the optical image measurement device according to the first embodiment, inform an alarm while preventing irradiation of the laser beam on the measured object when the light amount of the laser beam exceeds the specified upper limit.

The optical image measurement device 1 according to the present embodiment is configured such that an alarm part 353 and an irradiation prevention part 354, which are shown by dashed lines in FIG. 2, are added to the optical image measurement device according to the first embodiment. Moreover, the storage 312 stores a specified upper limit. Here, the specified upper limit may be the same as the upper limit in the first embodiment, or may be a limit value of the light amount adjustable by the light amount adjustment part 351 (a value greater than the upper limit threshold of the light amount).

The controller 310 makes adjustments such that the signal light passes through the light path L and is irradiated on the photodiode 105 by returning the galvanomirror 107A to the reference position and changing the direction of the galvanomirror 107B.

The photodiode 105 measures the light amount of the irradiated signal light. The photodiode 105 then outputs the measurement result to the light amount adjustment part 351, alarm part 353 and irradiation prevention part 354.

The light amount adjustment part 351 compares the upper limit stored in the storage 312 with the measurement result output from the photodiode 105. If the light amount adjustment part 351 has determined that the measurement result exceeds the upper limit, it sends a notification to the alarm part 353 and irradiation prevention part 354, indicating that the measurement result exceeds the upper limit. Moreover, if the light amount adjustment part 351 has determined that the measurement result exceeds the upper limit, it does not perform the light amount adjustment operation because the light amount cannot be adjusted.

The alarm part 353, upon receipt of the above notification from the light amount adjustment part 351, displays an alarm on the display 340A to inform the operator. The alarm part 353 corresponds to the "alarm part" in the present invention.

On the other hand, the irradiation prevention part 354, upon receipt of the above notification from the light amount adjustment part 351, controls either or both of the retinal camera unit 100 and the OCT unit 200 so as to prevent irradiation of the signal light on the eye E (measured object). Here, the method of preventing irradiation of the signal light on the eye E may be any method that avoids the entrance of the signal light into the eye E. As a specific example thereof, there exist configurations that stop the output of the low coherence light source 201, that fix the direction of the galvanomirror 107B such that the signal light passes through the light path L targeting the photodiode 105, or that insert a blocking object in the light path of the signal light, etc. The irradiation prevention part 354 corresponds to the "irradiation prevention part" in the present invention.

As described above, the optical image measurement device 1 according to the present embodiment is configured so as to inform an alarm to the operator while preventing irradiation of the signal light on the eye E when the light amount of the signal light exceeds the upper limit. Consequently, the measured object can be reliably protected and the safety can be improved.

Moreover, according to such an optical image measurement device 1, when the light amount of the signal light has exceeded the upper limit, the operator receiving the information of the alarm can recognize the situation as such and implement countermeasures to ensure safety.

The optical image measurement device 1 according to the above embodiment has both the alarm part 353 and the irradiation prevention part 354; however, the optical image measurement device 1 may be one that has either one of the alarm part 353 and the irradiation prevention part 354. Even in this case, there is also an effect of improving the safety.

In the above description, a configuration has been described in which an alarm is informed by the alarm part 353 and/or irradiation of the signal light on the eye E is prevented by the irradiation prevention part 354 when the upper limit has been exceeded. On the other hand, the configuration may be such that the light amount adjustment part 351 stores a specified lower limit, and an alarm is informed and/or irradiation of the signal light is prevented when the light amount of the signal light is below the lower limit.

Third Embodiment

The third embodiment of the optical image measurement device according to the invention will be described. This embodiment is configured to adjust the light amount of the signal light using the maximum brightness of the formed tomographic image (the maximum pixel value in the tomographic image) in the image formation mode. As such, in this embodiment, the light amount adjustment using the maximum brightness of the tomographic image in the image formation mode is explained. As premises for the following description, in the optical image measurement device 1, the operational mode has been switched to the image formation mode by the mode switching part 352.

The optical image measurement device 1 according to the present embodiment is configured such that a maximum brightness acquisition part 355, which is shown by dashed lines in FIG. 2, is added to the optical image measurement device according to the first embodiment.

The storage 312 stores the lower limit threshold of the maximum brightness (maximum brightness threshold) of a tomographic image.

The maximum brightness acquisition part 355 derives the pixel value for each pixel of the tomographic image formed by the image forming part 320 and defines the maximum value among the derived pixel values as the maximum brightness of that tomographic image. The maximum brightness acquisition part 355 then outputs the derived maximum brightness of the tomographic image to the light amount adjustment part 351.

The light amount adjustment part 351 compares the maximum brightness of the tomographic image input from the maximum brightness acquisition part 355 with the maximum brightness threshold stored in the storage 312. The light amount adjustment part 351 then increases the light amount of the low coherence light source 201 if this maximum brightness is below the maximum brightness threshold.

Moreover, the configuration may be such that the alarm part 353 is provided and the alarm part 353 informs an alarm if it is determined by the light amount adjustment part 351 that the maximum brightness is below the maximum brightness threshold.

As described above, the optical image measurement device 1 according to the present embodiment is configured so as to increase the light amount of the laser beam output from the low coherence light source 201 if the maximum brightness of the tomographic image is below the predetermined lower limit threshold (maximum brightness threshold).

According to such an optical image measurement device, it is possible to easily adjust the light amount of the laser beam in order to prevent degradation of the image quality of the tomographic image.

Moreover, in the present embodiment, a configuration has been described in which the light amount is adjusted and/or an alarm is informed based on the maximum brightness of the tomographic image for one eye. On the other hand, the following configuration may be employed. First, considering the individual differences of the eye, the maximum brightness of the tomographic image upon examination of a plurality of eyes is stored in the storage 312. Meanwhile, the maximum brightness of the tomographic image in this examination may be the maximum brightness of any one of the tomographic images acquired upon examination of each eye, or the average value from the specified number of tomographic images upon examination of each eye may be derived. Furthermore, the light amount adjustment part 351 calculates the average value from the maximum brightness value of the tomographic image in the latest examination to the maximum brightness value of the tomographic image in the examination at a specified time before, and compares this average value with the maximum brightness threshold. When it is determined that this average value is below the maximum brightness threshold, the light amount is adjusted by the light amount adjustment part 351 and/or an alarm is informed by the alarm part 353. By having such a configuration, the influence of the individual differences of the eye can be mitigated and degradation of the image quality of the tomographic image can be more effectively avoided.

Here, in the description of each embodiment and modification example above, for the purpose of illustration, the light amount adjustment part 351, mode switching part 352, alarm part 353 and irradiation prevention part 354 are each separately described, while also being described separately from the controller 310. However, in practice, the light amount adjustment part 351, mode switching part 352, alarm part 353 and irradiation prevention part 354 are configured so as to be included in the controller 310. Moreover, the maximum brightness acquisition part 355 is also described separately from the image-processing part for the purpose of illustration; however, in practice, the maximum brightness acquisition part 355 may be configured so as to be included in the image-processing part 330.

EXPLANATION OF SYMBOLS

1 Optical image measurement device
100 Retinal camera unit
101 Objective lens
102 Condenser lens system
103 Dichroic mirror
104 Deflection mirror
105 Photodiode
106 Condenser lens system
107 Scan unit
107A, 107B Galvanomirror
108 Deflection mirror
109 Condenser lens system
110 Observation and imaging optical system
200 OCT unit 201 Low coherence light source
202 Isolator
203 Optical coupler
204 Diffraction grating
205 Condenser lens system
206 Line CCD (CCD)
207 Condenser lens system
208 Reference mirror
300 Arithmetic and control unit
310 Controller
312 Storage
351 Light amount adjustment part
352 Mode switching part
353 Alarm part
354 Irradiation prevention part
355 Maximum brightness acquisition part
E Eye
Ef Fundus oculi

What is claimed is:

1. An optical image measurement device, comprising:
a light source that generates a laser beam;
a light amount adjustment part that adjusts light amount of the laser beam generated by said light source;
a scanning part that scans said laser beam on a measured object by changing irradiation position of said laser beam on said measured object by changing the direction of a galvanomirror;
a detection part that detects said laser beam reflected by said measured object;
an image formation part that forms an image of said measured object based on the detection result obtained by said detection part;
a light amount measuring part that is placed outside light path of said laser beam irradiated on said measured object and is capable of measuring the light amount; and
a mode switching part that alternatively switches between two modes: an image formation mode for forming an image of said measured object and a light amount measurement mode for measuring the light amount of said laser beam; characterized in that:
when the mode is switched to said light amount measurement mode by said mode switching part,
said scanning part changes the direction of said galvanomirror so that said laser beam is irradiated toward the light amount measuring part placed outside the light path;
said light amount measuring part measures the light amount of said input laser beam; and
said light amount adjustment part previously stores a specified light amount range, and adjusts the light amount of the laser beam generated by said light source such that the light amount measured by the said light amount measuring part falls within said specified range.

2. The optical image measurement device according to claim 1, characterized in that said light amount adjustment part previously stores the upper and lower limits of the light amount as said specified range and compares the light amount measured by said light amount measuring part with each of said upper limit and said lower limit, and when said measured light amount is above said upper limit, then reduces the light amount of the laser beam generated by said light source, and when said measured light amount is below said lower limit, then increases the light amount of the laser beam generated by said light source.

3. The optical image measurement device according to claim 1, characterized in that:
said light amount adjustment part previously stores the upper limit of the light amount of said laser beam as said specified range and compares the light amount measured by said light amount measuring part with said upper limit; and
further comprising an alarm part that informs an alarm when said measured light amount is above said upper limit.

4. The optical image measurement device according to claim 1, characterized in that:
said light amount adjustment part previously stores the upper limit of the light amount of said laser beam as said specified range and compares the light amount measured by said light amount measuring part with said upper limit; and
further comprising an irradiation prevention part that prevents the irradiation of said laser beam on said measured object when said measured light amount is above said upper limit.

5. The optical image measurement device according to claim 1, further comprising a maximum brightness acquisition part that acquires the maximum brightness of the image formed by said image formation part, characterized in that
said light amount adjustment part previously stores the maximum brightness threshold for the lower limit of the maximum brightness of the image as said specified range and compares the maximum brightness acquired by said maximum brightness acquisition part with said maximum brightness threshold, and when said maximum brightness is below said maximum brightness threshold, then adjusts the light amount of the laser beam generated by said light source to fall within said specified range.

6. The optical image measurement device according to claim 1, further comprising an operation part that is used for initiating the irradiation of said laser beam on said measured object, characterized in that:
said mode switching part switches, corresponding to the operation of said operation part, the mode to said light amount measurement mode to allow said light amount measuring part to measure the light amount of said laser beam, and subsequently, if the light amount initially measured by said light amount measuring part falls within said specified range, or if the light amount of said laser beam is adjusted by said light amount adjustment part, then switches the mode to said image formation mode to initiate the forming of the image of said measured object.

7. An optical image measurement device, comprising:
a light source that generates a low coherence light;
a light amount adjustment part that adjusts light amount of said low coherence light generated by said light source;
an interference light detection part that divides said low coherence light into signal light and reference light, scans said signal light on a measured object by changing irradiation position of said signal light on said measured object by changing the direction of a galvanomirror, superposes said signal light reflected by said measured object and said reference light travelling through reference light path to generate interference light, and detects said interference light;
a tomographic image formation part that forms a tomographic image of said measured object based on the detection result obtained by said interference light detection part;

a light amount measuring part that is placed outside light path of said signal light irradiated on said measured object and is capable of measuring light amount; and a mode switching part that alternatively switches between two modes: an image formation mode for forming an image of said measured object to be measured and a light amount measurement mode for measuring the light amount of said signal light; characterized in that:

when the mode is switched to said light amount measurement mode by said mode switching part, said interference light detection part changes the direction of said galvanomirror so that said signal light is irradiated toward the light amount measuring part placed outside the light path;

said light amount measuring part measures the light amount of said input signal light; and said light amount adjustment part previously stores specified range of light amount, and adjusts the light amount of the low coherence light generated by said light source such that the light amount measured by said light amount measuring part falls within said specified range.

* * * * *